US005632720A

United States Patent [19]

Kleitz

[11] Patent Number: 5,632,720

[45] Date of Patent: May 27, 1997

[54] MAGNETIC MASSAGE WAND

[76] Inventor: Cheltón R. Kleitz, P.O. Box 2063/301 N. 61st St., Kansas City, Kans. 66110

[21] Appl. No.: 410,918

[22] Filed: Mar. 27, 1995

[51] Int. Cl.$^6$ ................................ A61N 2/00; A61N 2/08

[52] U.S. Cl. .................................................. 601/15; 600/9

[58] Field of Search ................................ 601/15, 18, 19, 601/22, 84, 112; 600/9, 11, 13, 14, 15

[56] References Cited

U.S. PATENT DOCUMENTS

| | | | |
|---|---|---|---|
| 4,162,675 | 7/1979 | Kawada | 601/112 |
| 4,489,711 | 12/1984 | Latzke | 600/9 |
| 4,549,532 | 10/1985 | Baermann | 600/9 |
| 4,727,857 | 3/1988 | Horl | 600/9 |
| 4,744,350 | 5/1988 | Sato | 601/15 |
| 4,846,159 | 7/1989 | Anzai | 601/19 |
| 5,277,692 | 1/1994 | Ardizzone | 600/9 |

FOREIGN PATENT DOCUMENTS

| | | | |
|---|---|---|---|
| 253398 | 1/1988 | European Pat. Off. | 600/15 |
| 2510173 | 9/1976 | Germany | 600/9 |
| 4-53567 | 2/1992 | Japan | 600/9 |
| 8203177 | 9/1982 | WIPO | 600/9 |

*Primary Examiner*—Robert A. Hafer
*Assistant Examiner*—Brian E. Hanlon

[57] ABSTRACT

A magnetic massage wand apparatus with a motorized revolving wand including magnetic units aligned and spaced to obtain constantly alternating polarity fields at 90 degrees angles about the wand creating a general therapeutic effect of magnetism. The wand is operated by waving or holding it above or near the body tissue, so that blood circulation is effectively enhanced due to the alternating magnetic polarity occurring at a rapid and consistent rate which therapeutically effect blood vessels to increase blood flow irrespective of the orientation of any blood vessel with respect to the magnetic wand or how deep in the body the blood vessel may be.

4 Claims, 11 Drawing Sheets

FIG. 3
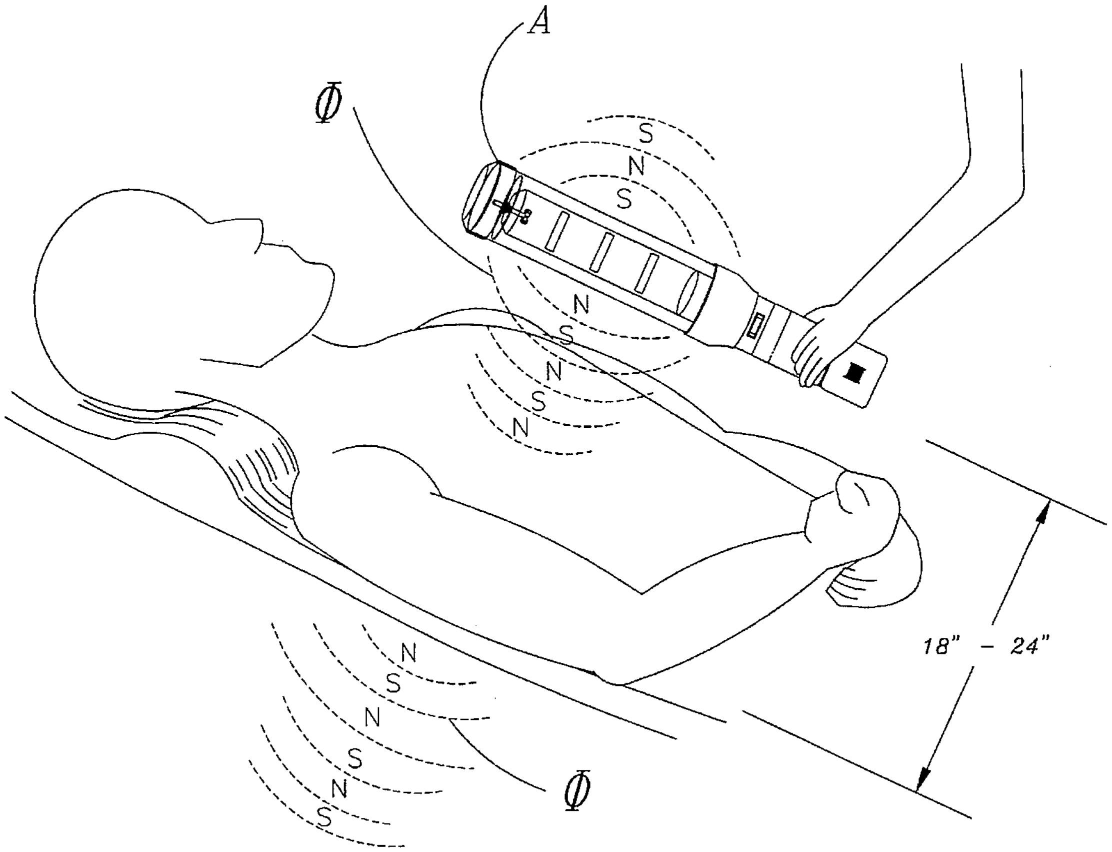
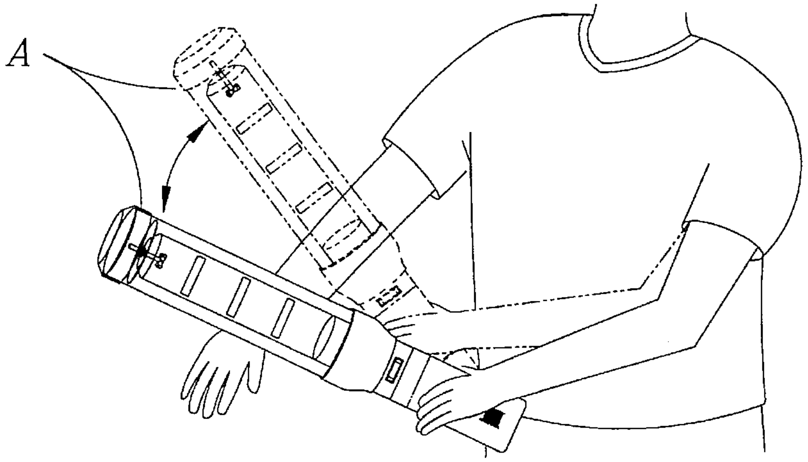
FIG. 4

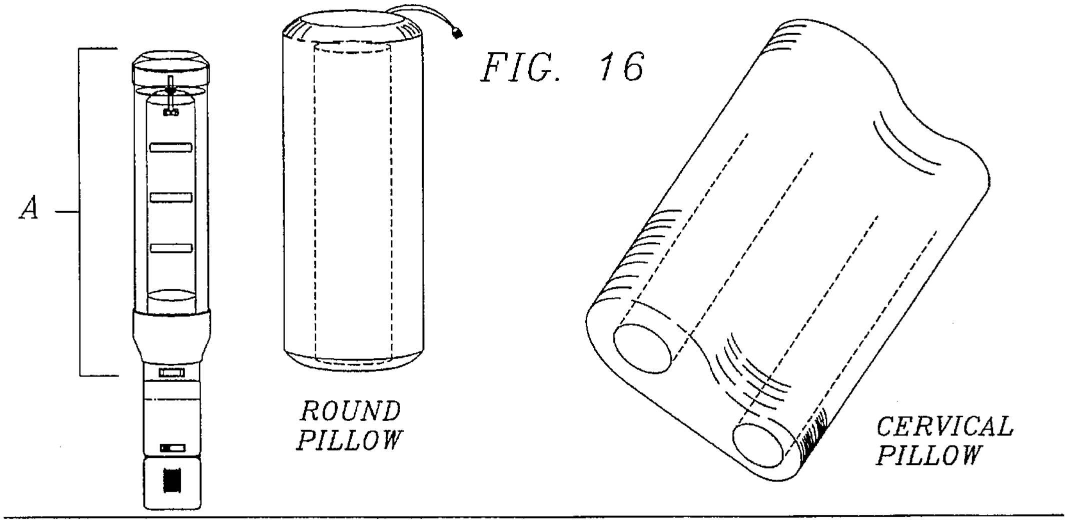
FIG. 16
DIFFERENT ROLLER SIZES & SHAPES
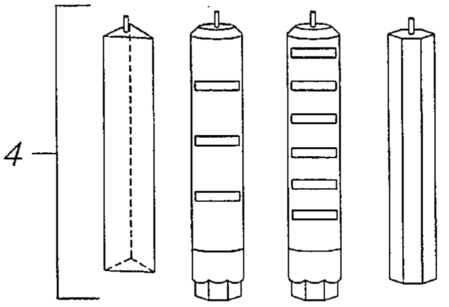
FIG. 17
MAGNETIC SHAPE
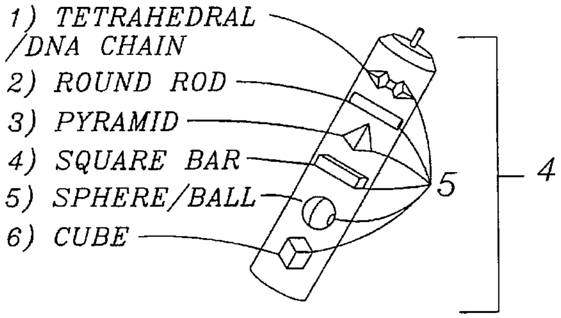
FIG. 18
STATIONARY AND FLEXIBLE STANDS
FIG. 19
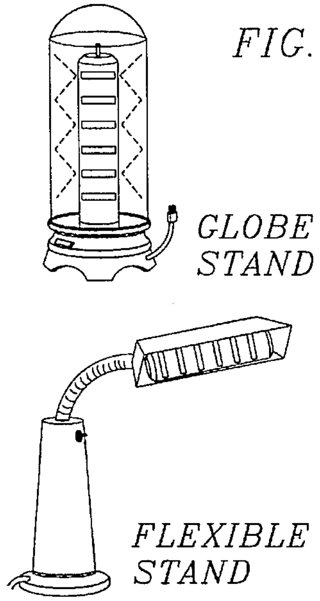
MAGNETIC WAND INCORPORATED IN FURNITURE AND THERAPEUTIC BEDS & TABLES
FIG. 20
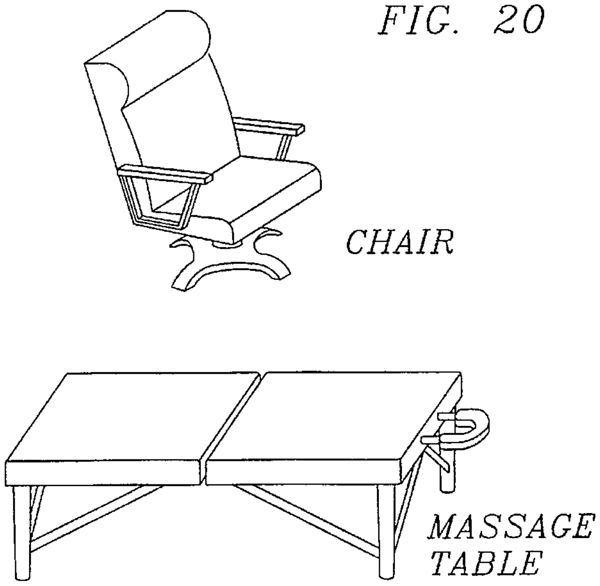

MAGNETIC MASSAGE WAND

BACKGROUND OF THE INVENTION

Various attempts have been made to provide therapeutic pads and massage devices with magnetic alternating polarities to increase blood flow and therefore accelerate healing of injured body parts. The technology is based on principles of electricity and magnetism set forth in Faraday's Law of Magnetic Induction and the Hall Effect. Basically, these principles establish the fact that charged particles experience a force acting upon them when they move through a magnetic field in a perpendicular direction. Since human blood is replete with ions and electrolytes, it is an ideal carrier of charged particles. A blood vessel exposed to a proper alignment of alternating magnetic fields could experience an induced voltage of sufficient strength to produce a mild alternating current which could generate enough heat to cause a widening of the blood vessel and thus an increase in blood flow.

In U.S. Pat. No. 4,489,711 of Latzke, using a pad consisting of alternating stripes of North and South magnetic poles are unidirectional in pole orientation. Latzke '711 provides parallel stripe-shaped poles in a linear arrangement that do not exhibit therapeutic effects on blood vessels that are not extending substantially traversely thereto.

In U.S. Pat. No. 4,549,532 of Baermann, using a pad consisting of either concentric rings or radial sectors with alternating polarities are provided. However, with respect to the concentric ring configuration of Baermann '532, the effective orientation for the concentric ring design is limited because of the assumption that all blood vessels will cross through the center of the device. The Baermann '532 device becomes progressively less effective as blood vessels are positioned away from the center until the device is non-effective at its peripheral outer ring, where a blood vessel will only traverse one pole with no increase in blood flow.

In U.S. Pat. No. 5,277,692 of Ardizzone, using a flexible pad consisting of an active surface with permanent magnetic particles embedded therein with said magnetic particles forming individual contiguous magnetic North and South polarity zones of opposite polarity being oriented so that at least one blood vessel will be in contact with alternate polarity zones irrespective of where said blood vessel is located while said blood vessel traverses any portion of said flexible pad. Although Ardezzone '692 has overcome the limitations of Latzke's '711 and Baermann's '532 pad devices, all of said magnetic pads have a limitation of depth of magnetic field, speed of alternating polarity working to increase the blood flow, and have to be applied to the skin.

In U.S. Pat. No. 4,846,159 of Masatsugu Anzai, Fukuoka; Takeo Imoto, Settsu, both of Japan, using a massage apparatus consisting of at least two balls which are provided with a number of projections on the outer periphery thereof and a case for enclosing and retaining the balls in rotatable state and in attachable detachable manner. Further, when a ball or balls having magnetism qualifies, are used, in addition to the general effect due to the magnetism, an advantage that blood circulation is effectively enhanced due to an alternating magnetic field can be obtained by rolling the magnetic balls across the skin.

The advantage of the present invention is that it takes into account all the random positions of the blood vessels relative to the location of the device with the addition of increased depth of magnetic field through all the soft tissue, muscle tissue, and dense bone tissue. It works as well for a blood vessel traversing anywhere in the body within 18 to 24 inches of the device. Further, unlike the Anzai-Imoto '159, using magnetic balls to roll across the skin to create alternating magnetic fields, the present invention incorporates a motorized revolving wand that includes magnetic units aligned and spaced to obtain constantly alternating polarity at 90 degrees, plus or minus angles from the wand creating a general therapeutic effect of magnetism; operated by waving or holding the wand above or near the body tissue, not needing to touch or come in contact with the skin. Blood circulation is effectively enhanced due to said alternating magnetic polarity at a rapid and consistent rate, which therapeutically effect blood vessels, causing an increase of blood flow irrespective of the orientation of any blood vessel with respect to the magnetic wand, no matter how deep the blood vessels may be positioned in the body.

OBJECTS OF THE INVENTION

Therefore it is an object of the present invention to provide a therapeutic motorized magnetic wand of constantly alternating polarity fields which is effective no matter where a blood vessel traverses anywhere in the body within 18 to 24 inches of the device without having to touch or roll across the skin.

SUMMARY OF THE INVENTION

The device of the present invention utilizes principles set forth in the Latzke '711, Baermann '532, Ardizzone '692. In the present invention, instead of utilizing flexible magnetic pads arranged in an alternating pattern of North (−) and South (+) polarity zones or poles applied to areas of the skin, or having to roll magnetic balls across the skin to create alternating magnetic fields as set forth in Anzai-Imoto '159, the new invention will generate with the motorized revolving wand, constantly alternating deep penetrating, North (−) and South (+) polarity fields at a rapid and consistent rate. When placed over an afflicted area of the human body, these alternating polarity fields have been shown to have a therapeutic effect. For example, the magnetic wand can be applied to musculo-skeletal bruises, sore muscles and joint pain for relief to the user from pain. These alternating polarity fields however, must be within 18 to 24 inches of said afflicted area, as to cause blood moving through the veins in the body to pass through the magnetic fields established by the polarity in an alternating field pattern. Considering the differences in the functionality, depth of intensity, and the ease of operation without having to touch the body, and that of the prior art, the proposed device of the present invention is an improvement over prior art that is substantial and not obvious.

BRIEF DESCRIPTION OF THE DRAWINGS

FIG. 3 and FIG. 4 are illustrations showing respective used states of the magnetic massage wand apparatus A shown in FIGS. 1 and 2, and depth of alternating magnetic fields, $\Phi$.

FIG. 16 to FIG. 20 are illustrations showing various forms and methods for using the magnetic massage wand apparatus of the present invention.

DETAILED DESCRIPTION OF THE INVENTION

Figure 1:
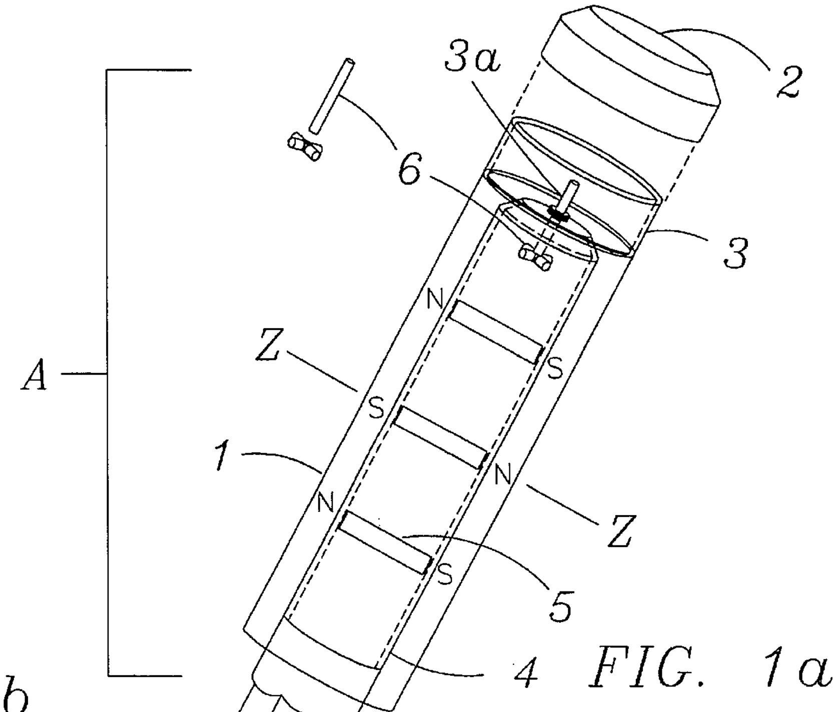
FIG. 1 is a perspective view of first embodiment of the magnetic massage wand apparatus of the present invention.
Figure 1:
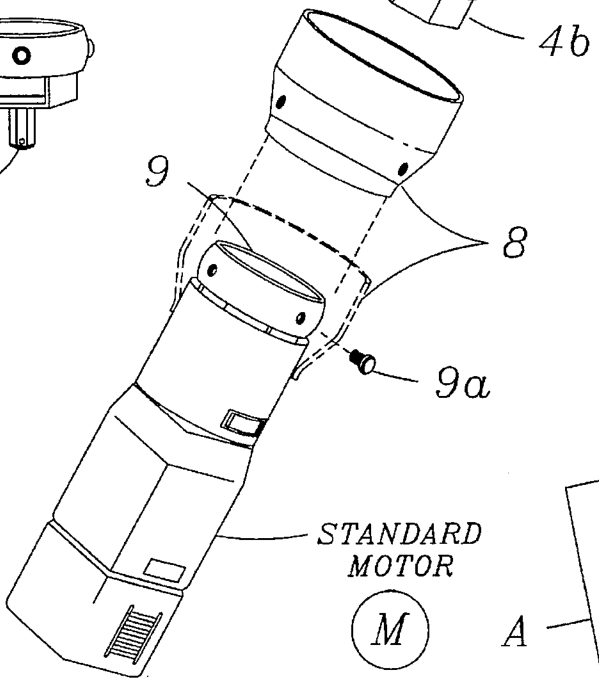
Figure 1A:
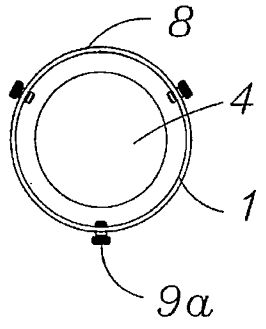
FIG. 1*a* is a topview of a portion of a first embodiment of the Magnetic Massage Wand apparatus of the present invention.
Figure 1B:
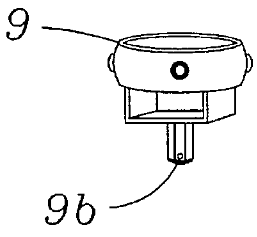
FIG. 1*b* is a perspective view of the connecting device to the standard small motor.
Figure 2:
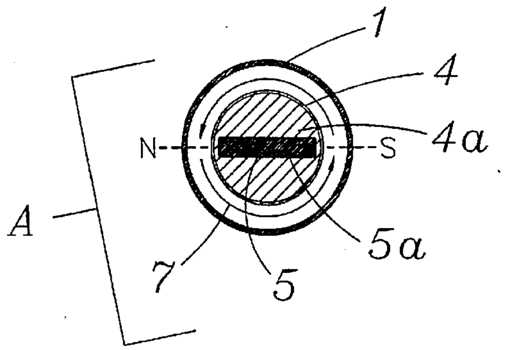
FIG. 2 is a cross sectional view along line z—z of FIG. 1, showing outside protective housing, magnet, and inner wand.
Figure 13:
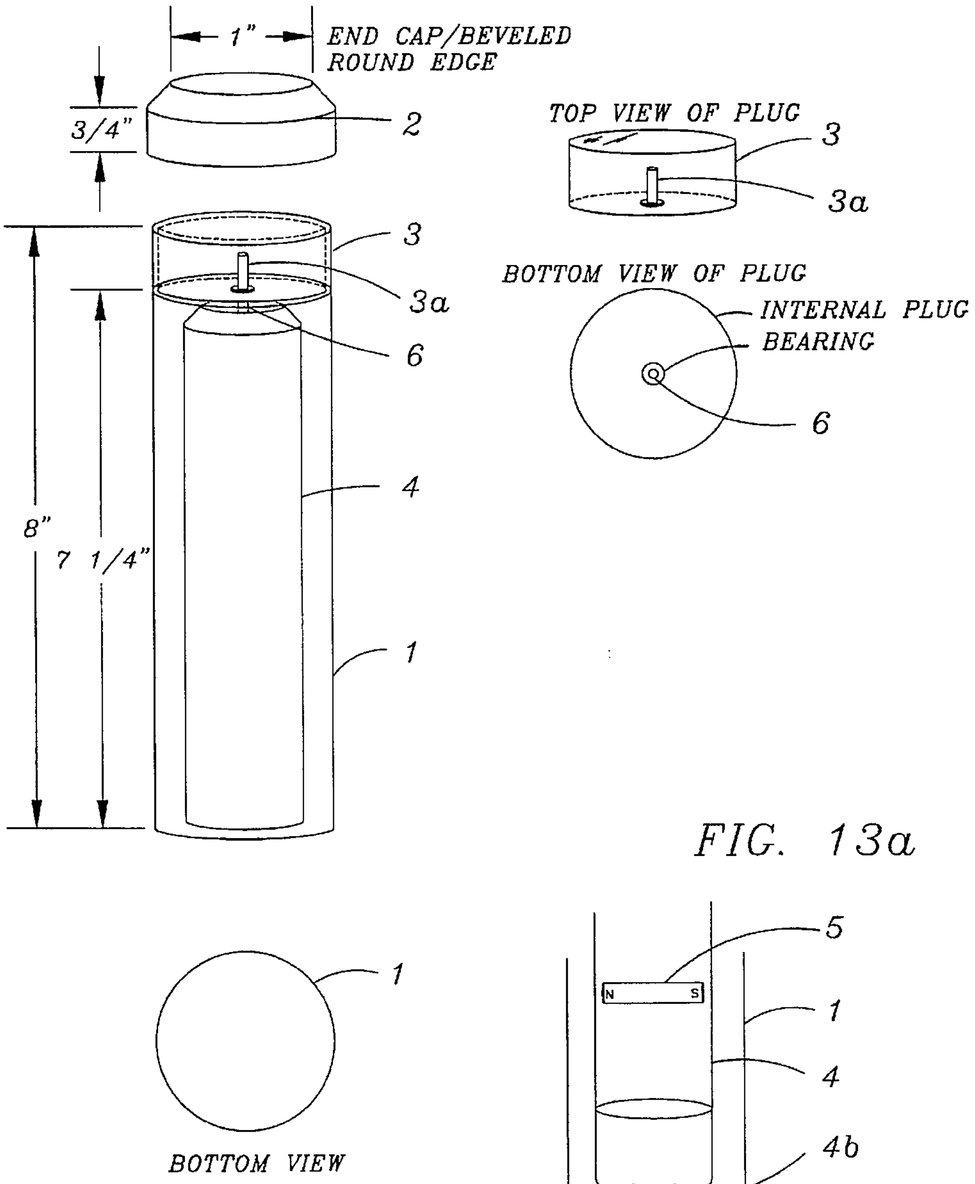
FIG. 13 is a side view of the present invention showing outside protective housing with inside revolving cylinder wand, plug, and cap.

Now referring to FIGS. 1 to 4, the first embodiment is described. Referring to FIGS. 1 and 2, numeral 1 denotes an outside protective stationary cylinder formed with synthetic resin such as styrel resin or acryl resin; that fits over magnetic wand 4. The protective outside cylinder 1 is open at both ends so as to allow easy attachment to a small standard motor with a round rubber or plastic housing 8, FIG. 13, enabling outside cylinder 1 to slip tightly into housing and be held with hot glue. On the other end of outside cylinder 1, FIG. 13, a tightly fitting round plug 3 is formed with synthetic resin or natural wood. Recessed in the center of this plug 3 is a ⅛ inch steel bearing 3*a*, which is available through most hobby shops. Once plug 3 is in place, an end cap 2 formed with synthetic resin in color to enhance the display appeal, will be snapped on to give a quality finish look.

The inner revolving wand 4 FIG. 2, is a molded solid cylinder formed with synthetic resin 4*a* such as acryl resin, AS resin, GPPS resin or styrel resin and may be made transparent or color may be added to enhance the display effect.

Figure 14:
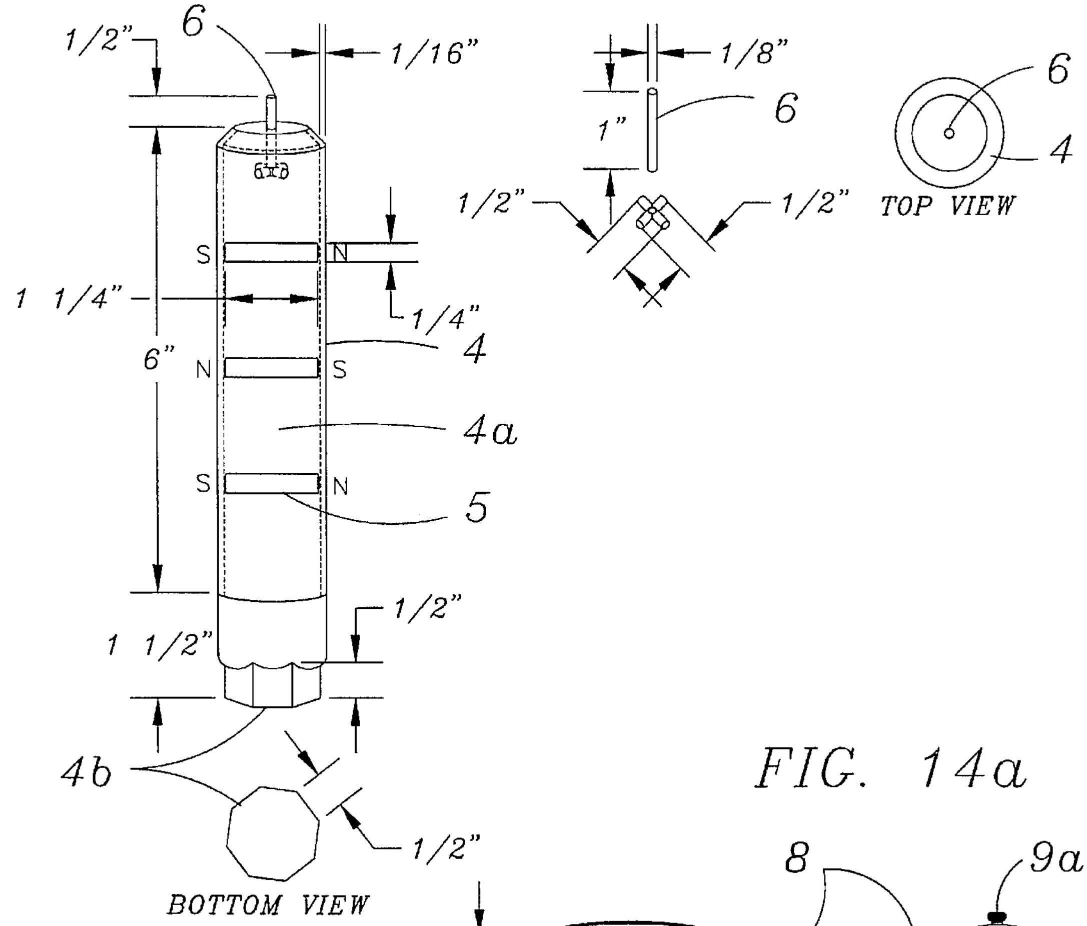
FIG. 14 is a full side view of the present invention showing inside revolving cylinder wand with top and bottom views.

Magnetic units 5 FIG. 2, made of either solid or molded synthesized resin and ferrite 5*a* with a therapeutic intensity of 950 to 1,050 gauss, are placed inside the molded wand, at the time the mold is poured, in parallel positions and spaced evenly at 1½ inches apart with all like magnetic North (−) poles and South (+) poles facing the same direction or alternating directions at 90 degree angles to the length of the wand 4, FIG. 1. At top end of inner revolving wand 4 FIG. 14, is a flared metal 2 inch long ⅛ inch diameter rod 6 placed in end of molded wand 4 protruding by ¾ inch out of center of the end of inner wand 4 allowing rod 6 FIG. 13, to insert easily into bearing 3*a* of plug 3 in order to stabilize revolving wand 4. At bottom end of inner revolving wand 4, FIG. 14, as part of said wand, an octagon shaped molded chuck 4*b* was formed as part of wand design in order to make an easy attachment to a standard motor.

Figure 13A:
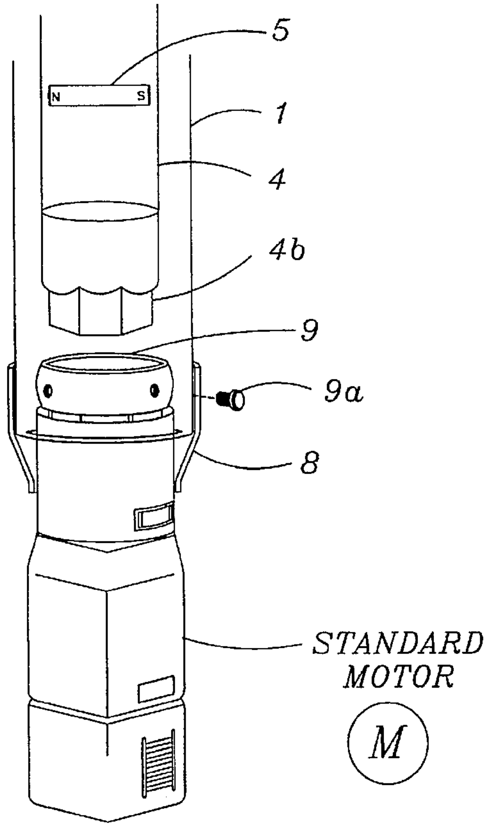
FIG. 13*a* is a side view of the present invention showing outside protective housing and inside revolving cylinder wand with octagon molded chuck and connecting devices to standard small motor.
Figure 14A:
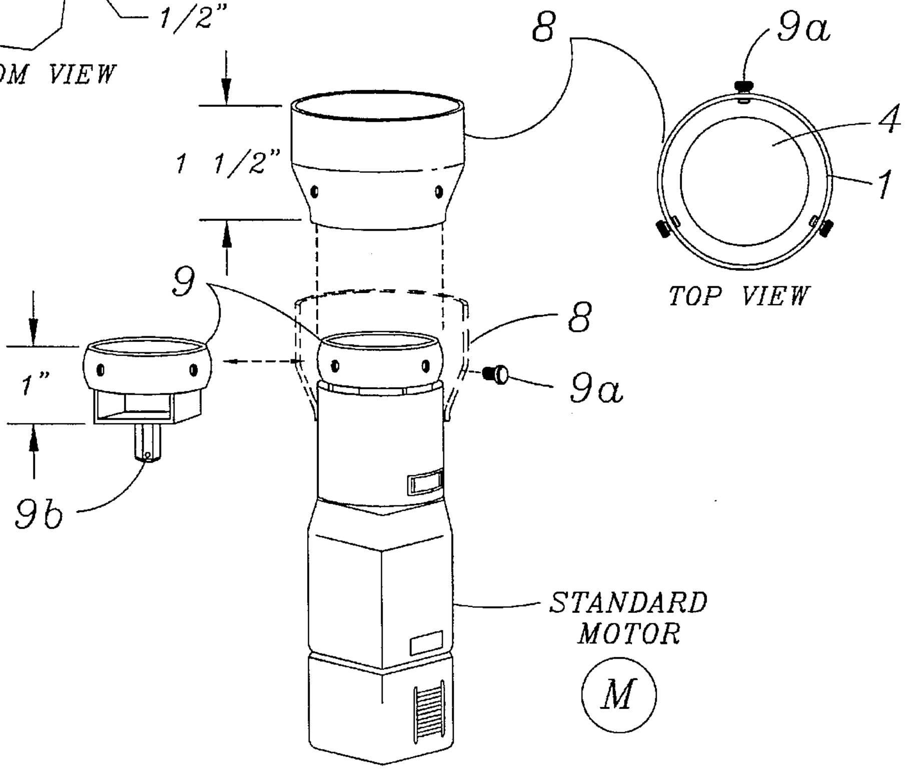
FIG. 14*a* is a side view of the present invention showing detail of connecting devices to standard small motor.

Inner revolving wand 4 with molded chuck 4*b* inserts into connecting device 9 FIG. 13*a* and held with three allan screws 9*a*. Square chuck 9*b* FIG. 14*a* is part of a standard small motor and when snapped together allows the small motor m, run on rechargeable batteries or plugged into standard 110 electric current, to create a variable speed of 3,000 to 5,000 R.P.M. which turns inner cylinder wand 4 in a revolving manner 7, FIG. 15 obtaining constantly alternating polarity fields Φ at a rapid and consistent rate maximizing therapeutic use to increase blood flow, wherein said blood vessels traverse within 18 to 24 inches of the magnetic wand A.

Figure 8:
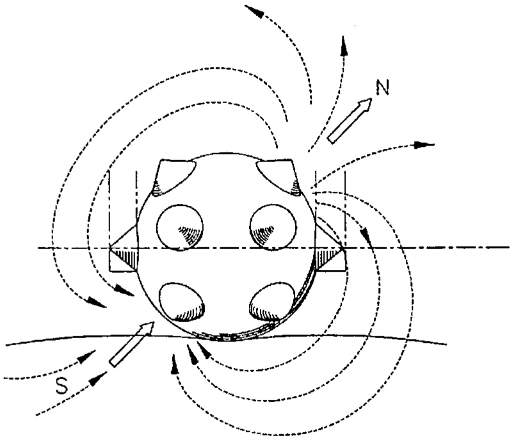
FIG. 8 and FIG. 9 are perspective views of one embodiment of prior art as noted in Anzai-Imoto, U.S. Pat. No. 4,846,159, showing functions of alternating magnetic fields in a massage apparatus device that rolls over the skin.
Figure 9:
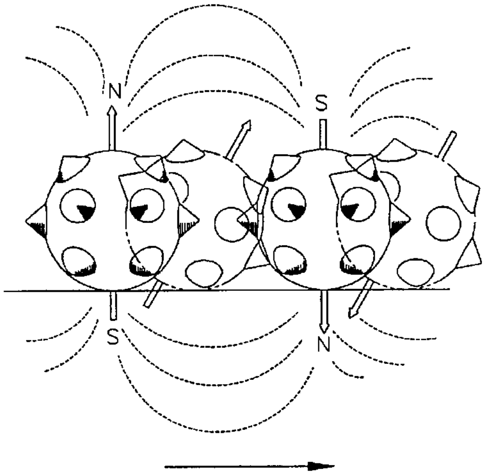
Figure 10:
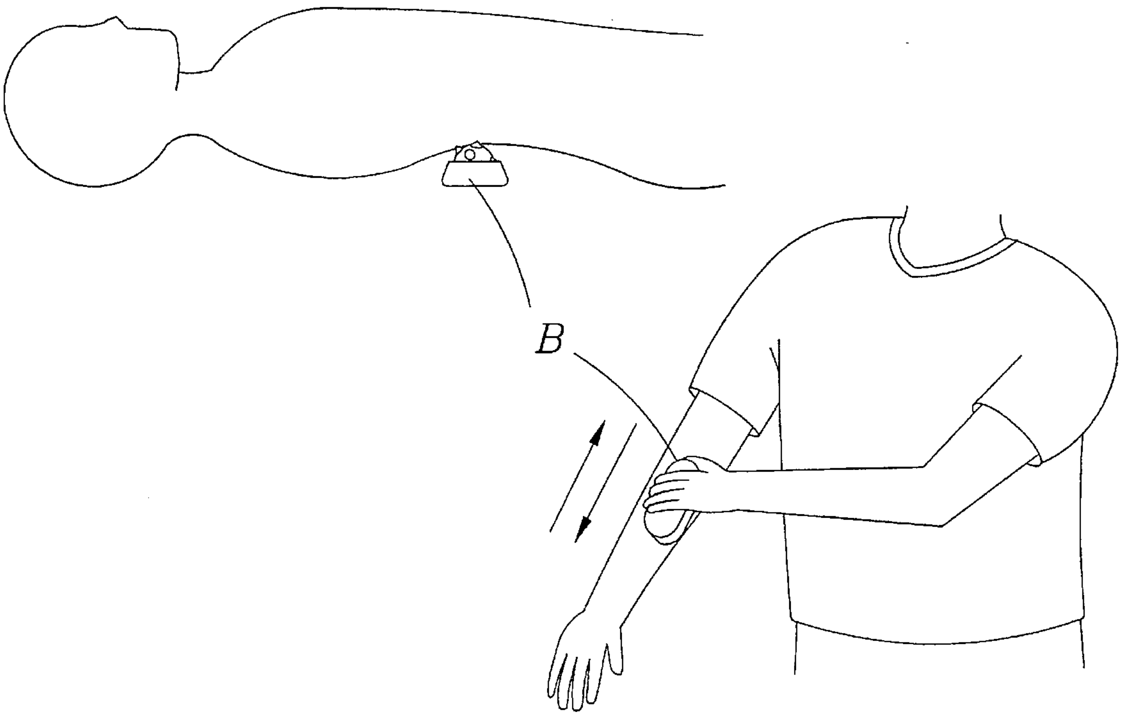
FIG. 10 is an illustration of a prior art device showing used state of the massage apparatus device B, encased, shown in FIGS. 8 and 9.

Referring to FIGS. 3 and 4 as illustrations showing respective used states of magnetic massage wand apparatus A shown in FIGS. 1 and 2. FIG. 3 shows someone, like a therapist, holding or waving the wand A over a person lying down. FIG. 4 shows a person holding or waving the wand A over themself while standing. Since a person can hold the magnetic wand A over any part of the body and not have to touch or roll across the skin to get a therapeutic effect of enhancing blood circulation with the alternating polarity fields Φ all the way through the body to a depth of 18 to 24 inches from the wand A, this is a great advantage for many therapists and individuals over the limitations of Anzai-Imoto's massage apparatus device B, FIG. 10. Even though FIGS. 8 and 9 are trying to show functions of alternating magnetic fields in a massage apparatus device B, it still has to roll over the skin and is also limited to the direction of the roll, the speed the operator rolls the device, and the difficulty in reaching or rolling over certain spots of the body.

Figure 5:
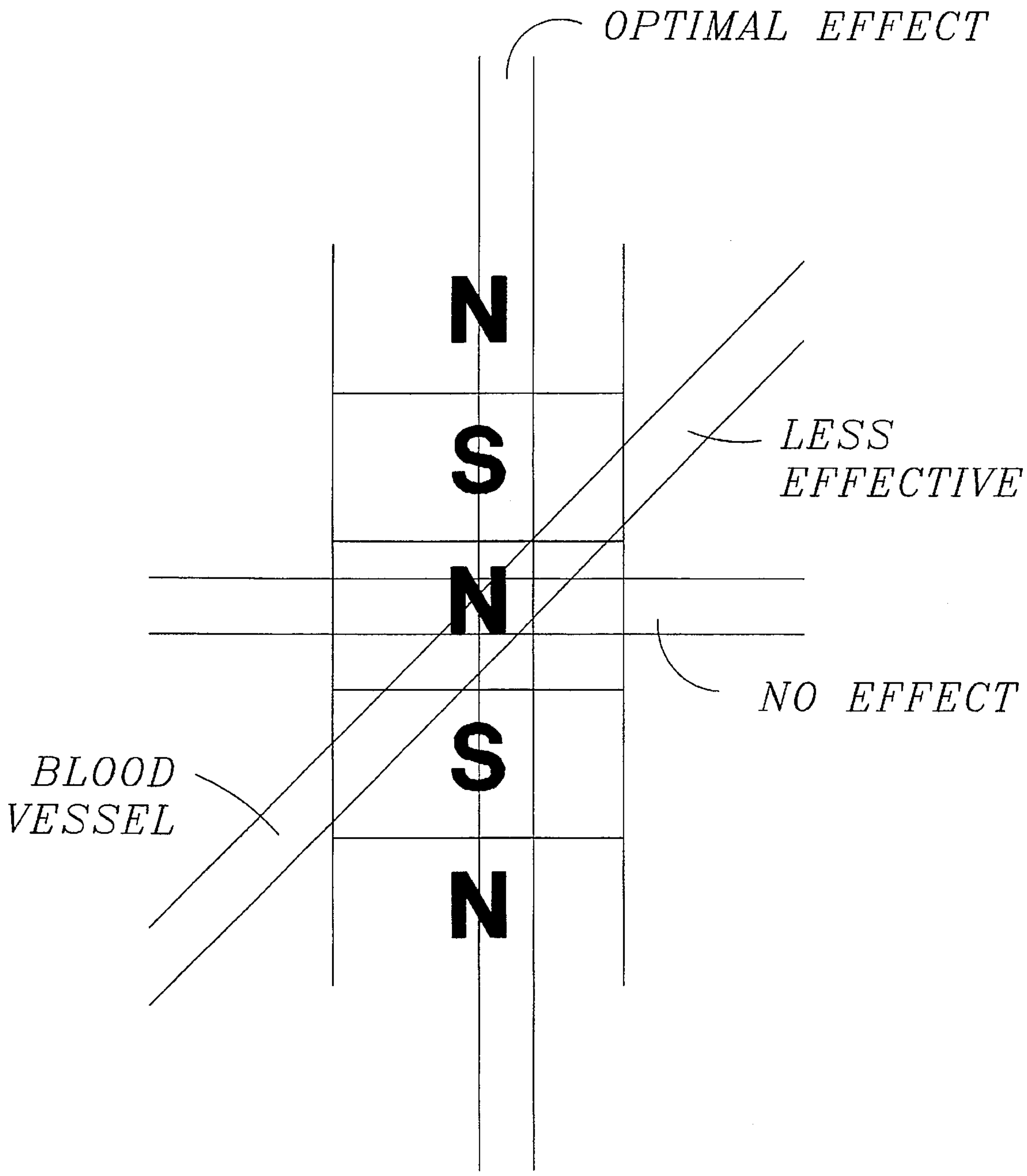
FIG. 5 is a top plan view of one embodiment of prior art as noted in Latzke, U.S. Pat. No. 4,489,711, showing various positions of blood vessels traversing the prior art pad device.
Figure 6:
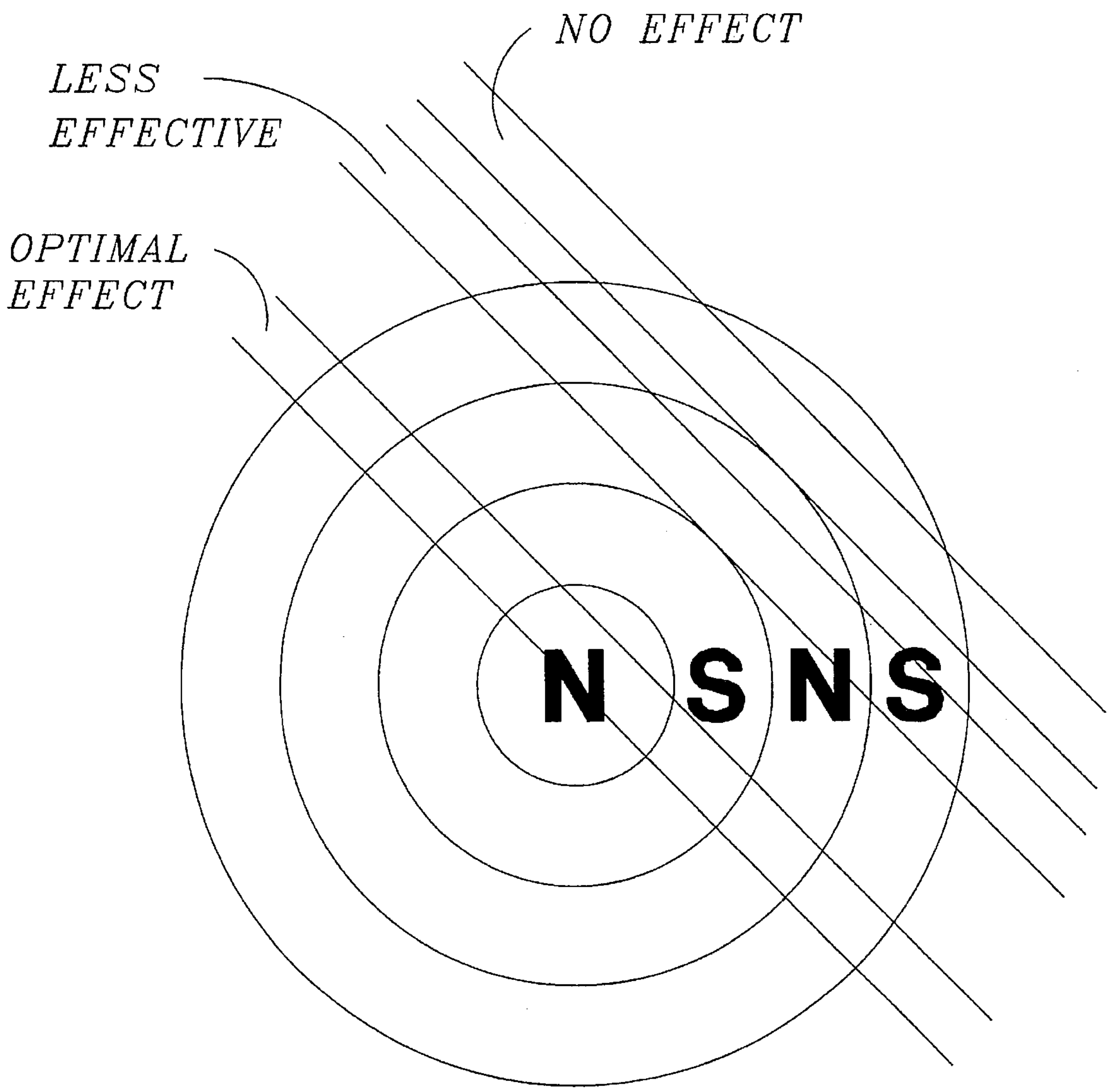
FIG. 6 is a top plan view of another embodiment of a prior art device, as noted in Baermann, U.S. Pat. No. 4,549,532, showing various positions of blood vessels traversing the prior art pad device.
Figure 7:
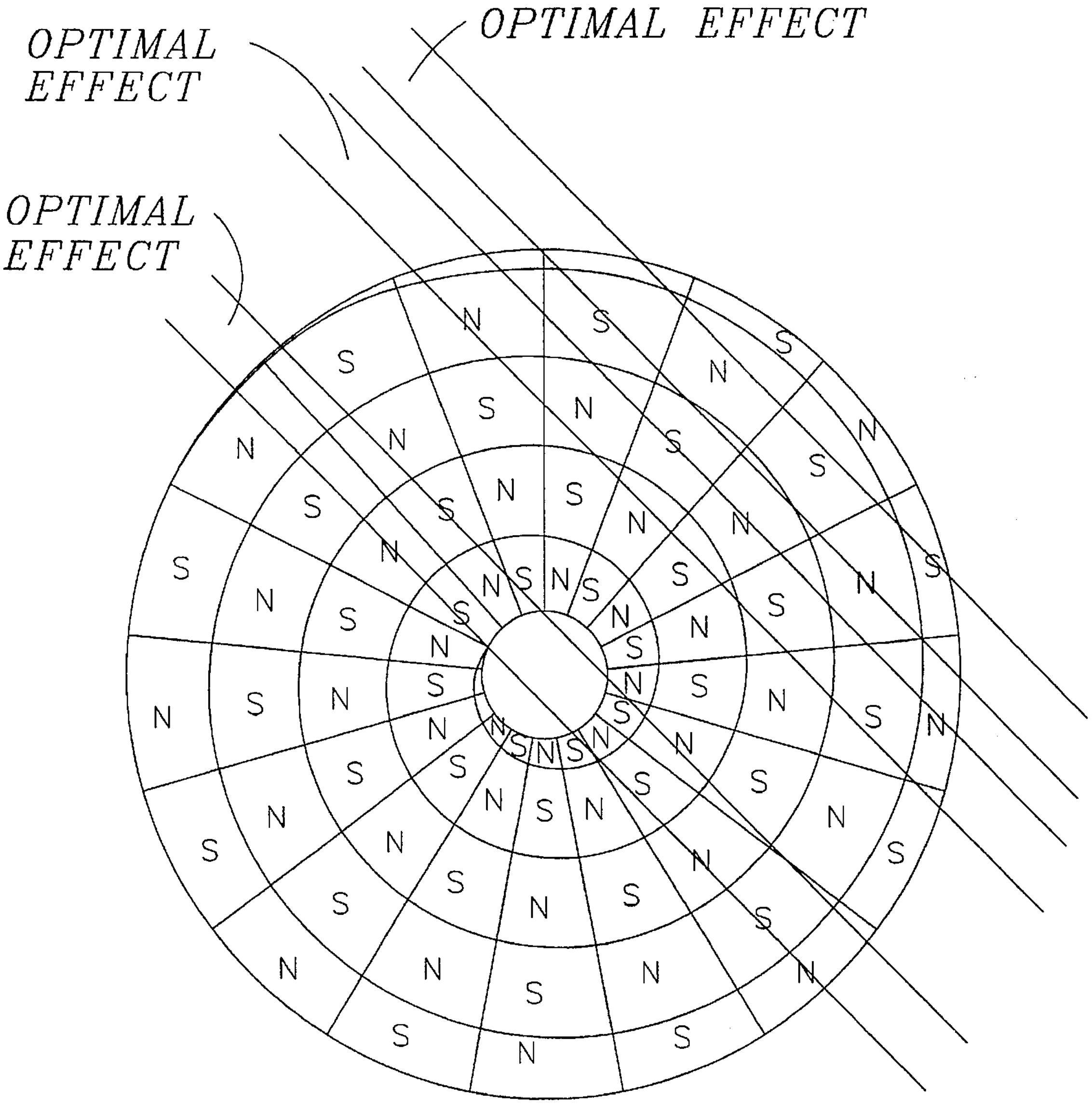
FIG. 7 is a top plan view of another embodiment of a prior art device, as noted in Ardizzone, U.S. Pat. No. 5,277,692, showing various positions of blood vessels traversing the best prior art pad device.
Figure 15:
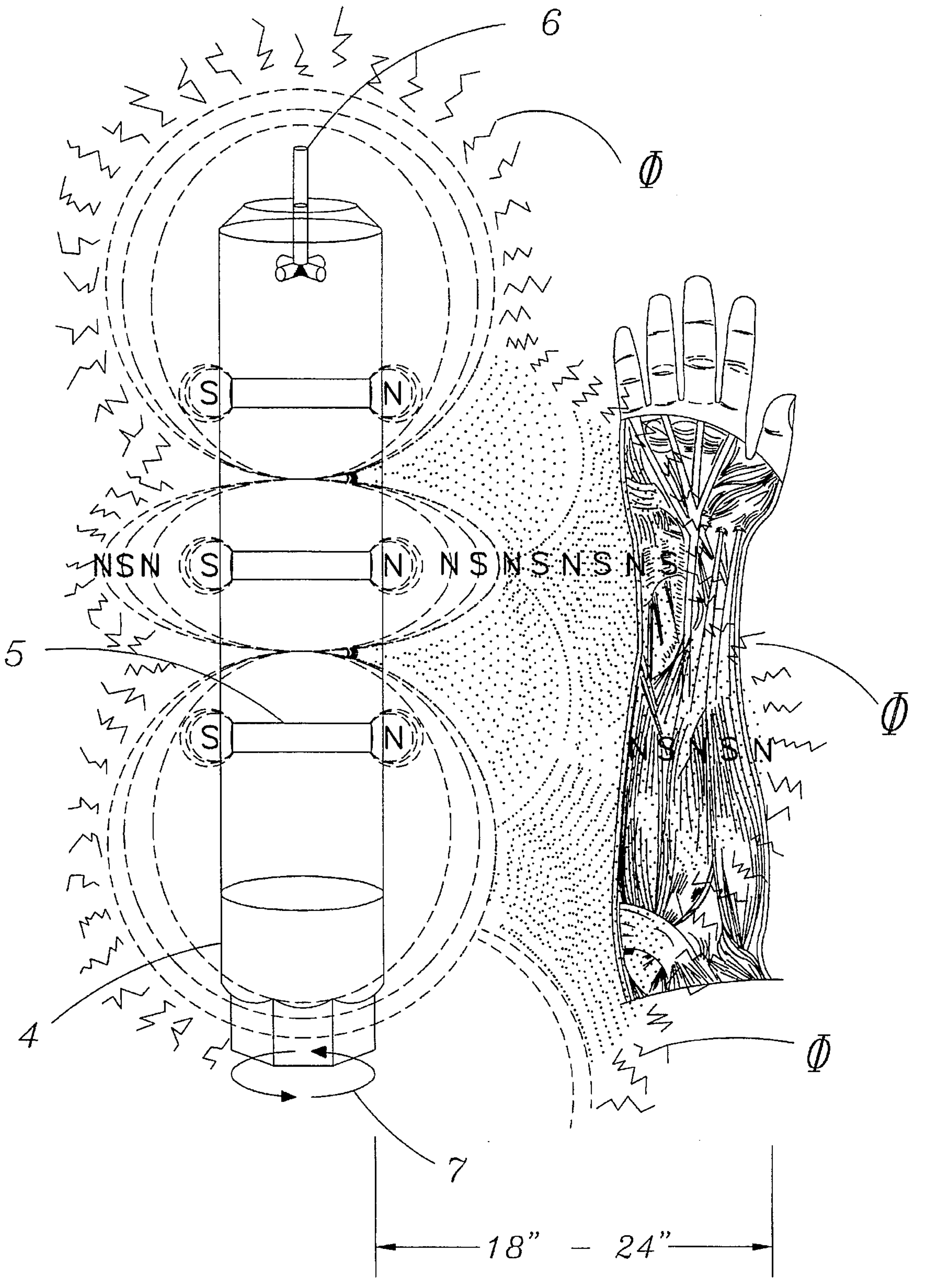
FIG. 15 is an illustration of the present invention showing depth of alternating magnetic fields Φ penetrating therapeutically 18 to 24 inches from the magnetic massage wand apparatus.

Referring also to FIGS. 5 to 7 comparing even the flexible magnetic pad devices of Latzke, FIG. 5, and Baermann, FIG. 6, trying to cover the various positions or directions of blood vessels traversing the prior art pad devices and how Ardizzone, FIG. 7, shows that his flexible magnetic pad device was able to cover the most directions and positions of blood vessels traversing the prior art pad device. All of these magnetic pad devices, FIGS. 5 to 7, show a definite limitation due to pad needing to be placed on the skin, limited depth of field on effectiveness, and speed of blood flow traversing the pad device. Even though pad devices can be worn long term, many times they are not placed over the right spot for the discomfort or are not able to penetrate some of the thick muscles and bone deep enough. The magnetic massage wand apparatus A does not have to touch or roll across the skin, but instead, it is just held or positioned above or near the body. FIG. 3 and FIG. 15 illustrate the present invention showing the depth of penetration of alternating therapeutic magnetic fields Φ radiating 18 to 24 inches from the magnetic massage wand apparatus A so that no matter how blood vessels are situated under the device, they therefore receive optimal effect.

Figure 11:
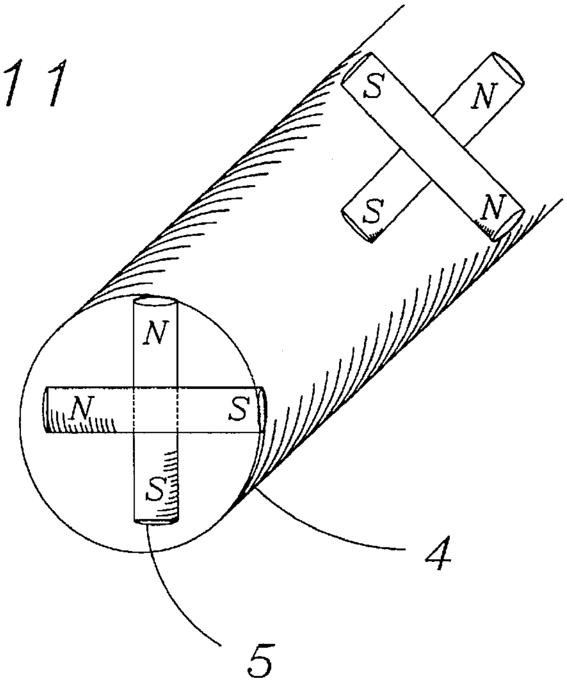
FIG. 11 is a perspective view showing a second embodiment of the present invention with magnets placed at two alternating positions.

FIG. 11 is a perspective view showing a second embodiment of the present invention with two magnets 5 placed so that the longitudinal axis of one magnet is at 90 degrees relative to the longitudinal axis of the other magnet. This orientation allows for the pole positions to have like polarities offset by 90 degree angles and opposite poles to be offset by 90 degrees and 180 degree angles, so as to create faster alternating fields.

Figure 12:
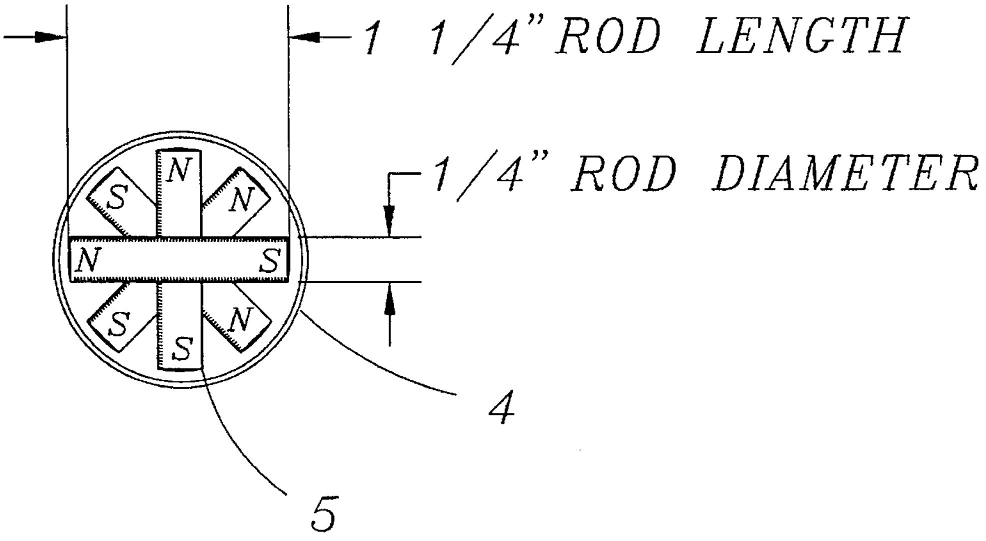
FIG. 12 is a cross sectional view showing a third embodiment of the present invention with magnets placed in various positions.

FIG. 12 is a perspective view showing a third embodiment of the present invention with four magnets 5 placed so that the longitudinal axis of one magnet is at 45 degrees relative to the longitudinal axis of the other magnets. This orientation allows for the pole positions to have like polarities offset by 90 and 45 degree angles and opposite poles to be offset by 45, 90 and 180 degree angles, so as to create the fastest alternating fields, generating a magnetic wave pattern resembling a spiral.

As noted in FIGS. 16 to 20 the present invention may also be constructed or placed in several various shapes of magnetics 5, FIG. 18, or may also display several various shapes or sizes of inner wand 4, FIG. 17; or may be inserted into a pillow FIG. 16; or may be placed in stationary globe or flexible holding device as illustrated in FIG. 19; or even placed in a chair backing or under a massage table as in FIG. 20.

In contrast to the prior art devices as shown in FIGS. 5 through 10 herein, the present invention as shown in FIGS. 1 through 4 and FIGS. 11 through 20 herein maximizes the therapeutic effects on blood vessels by increasing the blood flow by virtue of the exposure of the blood vessels to constantly alternating polarity fields, no matter how deep in body said vessels may be or direction said vessels may flow without having to touch or roll across the skin.

It is to be noted that other variations and modifications may be made to the present invention without departing from the spirit and scope thereof, as noted in the following claims.

I claim:

1. A motorized, magnetic massage wand for increasing circulation in blood vessels within 18 to 24 inches of said wand, said wand comprising:

a molded solid non-magnetic cylinder having a longitudinal axis and a diameter perpendicular to said axis;

a protective outside stationary shield placed about said solid non-magnetic cylinder, said shield being a hollow transparent cylinder made of non-magnetic synthetic resin having a diameter greater than that of said solid non-magnetic cylinder, one end of said shield housing an end plug with a ball bearing recessed with said plug, a rod having a first end located within said plug and extending through said bearing into said cylinder for stabilizing the movement of said cylinder;

an end cap located at said one end of said protective shield and covering said solid non-magnetic cylinder and said protective shield;

at least two magnetic units located within said solid non-magnetic cylinder, each said magnetic unit having a longitudinal axis, said magnetic units being evenly spaced 1½ inches apart and placed in said solid non-magnetic cylinder such that their longitudinal axes are perpendicular to the longitudinal axis of said solid non-magnetic cylinder and parallel to each other, said magnetic units being positioned so that all magnetic poles are aligned along lines running parallel to the longitudinal axis of said solid non-magnetic cylinder and a transverse axis of each unit is parallel to the longitudinal axis of said solid non-magnetic cylinder; and a motor contained with said wand and attached to said solid non-magnetic cylinder for rotating the solid non-magnetic cylinder about its longitudinal axis at a rapid and consistent rate to obtain constantly alternating polarity fields about the body;

whereby the circulation is increased by waving or holding said massage wand near the human body so that the blood flow in vessels within 18 to 24 inches of the wand is increased.

2. The magnetic massage wand of claim 1 wherein said magnetic units are made of a solid or molded synthesized resin and ferrite with a therapeutic intensity of 950 to 1050 gauss.

3. The magnetic massage wand of claim 1 wherein said solid non-magnetic cylinder is formed of a non-magnetic resin.

4. The magnetic massage wand of claim 1 wherein said motor turns said non-magnetic cylinder at a speed of 3000 to 5000 revolutions per minute for maximizing the therapeutic effect of the wand.

* * * * *